United States Patent [19]

Siray et al.

[11] Patent Number: 4,931,593

[45] Date of Patent: Jun. 5, 1990

[54] METHOD FOR PRODUCING TETRAPROPYLAMMONIUM BROMIDE

[75] Inventors: Mustafa Siray; Peter Kleinschmit, both of Hanau, Fed. Rep. of Germany

[73] Assignee: Degussa Aktiengesellschaft, Frankfurt am Main, Fed. Rep. of Germany

[21] Appl. No.: 325,938

[22] Filed: Mar. 20, 1989

[30] Foreign Application Priority Data

Mar. 31, 1988 [DE] Fed. Rep. of Germany ....... 3810953

[51] Int. Cl.$^5$ ............................................. C07C 87/30
[52] U.S. Cl. ................................................... 564/296
[58] Field of Search ....................................... 564/296

[56] References Cited

U.S. PATENT DOCUMENTS 3,965,178  6/1976  Johnson et al. ..................... 564/296

FOREIGN PATENT DOCUMENTS 0041621  12/1981  European Pat. Off. ............ 564/296
59-27854   2/1984  Japan ................................... 564/296
88/6152    8/1988  World Int. Prop. O. .......... 564/296

OTHER PUBLICATIONS

Shen, Chem. Abst., vol. 108, #166830b (1988).
Fieser et al., "Reagents for Organic Synthesis", p. 1110 (1967).

Primary Examiner—James H. Reamer
Attorney, Agent, or Firm—Beveridge, DeGrandi & Weilacher

[57] ABSTRACT

A method for producing tetrapropylammonium bromide by reacting tripropylamine with propyl bromide in a polar solvent at a temperature between 60° and 160° C.

1 Claim, No Drawings

METHOD FOR PRODUCING TETRAPROPYLAMMONIUM BROMIDE

The invention relates to a method for producing tetrapropylammonium bromide.

Tetrapropylammonium bromide is used as a reagent in the production of the zeolite ZSM-5 disclosed in U.S. Pat. No. 3,702,886 and European Patent No. 41,621.

It is known from the European Patent No. 41,621, page 1, line 15, that the quarternary ammonium compound tetrapropylammonium bromide is difficult to obtain.

Accordingly, there is a need for a simple and economical method to produce tetrapropylammonium bromide.

The object of the present invention is a method for producing tetrapropylammonium bromide characterized in that tripropylamine is reacted with propyl bromide in a polar solvent at a temperature between 60 and 160° C.

Among the suitable polar solvents are nitromethane, hexamethylphosphoric acid triamide, dimethylformamide or N, N'-dimethylpyrol.

The reaction period can range from 2 to 32, preferably 2 to 15 or 4 to 12 hours.

The preferred temperature of the reaction is 80° to 140° C., especially 100° to 130° C.

In a preferred implementation of the invention, the proportion of tripropylamine and propylbromide to the solvent may be 20 to 60%. This value is calculated as follows:

$$\frac{\text{ml of solvent}}{\text{ml of propylbromide + ml of tripropylamine}} \times 100 = \%$$

The method of the invention offers the advantage that upon cooling the solvent or the reaction mixture, 65% by weight of the product is obtained in crystalline and analytically pure form, in reference to the tripropylamine.

Without processing, the mother liquor can be used for the next batch.

The reaction product need not be recrystallized.

EXAMPLE 1

135 g (1.09 moles) of propyl bromide and 140 g (0.96 moles) of tripropylamine are heated together with 200 ml of dimethylformamide up to 130° C., in equipment provided with reflux condenser and thermometer, for 6 hours. The end point can be ascertained by the disappearance of the two phases formed from propyl bromide and dimethylformamide/tripropylamine and by the rise in temperature. The resulting solution is cooled and crystals of tetrapropylammonium bromide are precipitated. The crystalline product is filtered and dried.

Yield: 162 g (63% in reference to the tripropylamine).

EXAMPLE 2

135 g (1.09 moles) of propylbromide and 140 g (0.96 moles) of tripropylamine are combined with the mother liquor of Example 1 and are heated again for 6 hours to 130° C. Upon cooling the solution, crystals of tetrapropylammonium bromide precipitated.

Yield: 174 g (65% referred to the tripropylamine).

This mother liquor can be further used. By concentrating the mother liquor down to half the volume, another 50.8 g (19% in reference to tripropylamine) of tetrapropylammonium bromide can be isolated from the mother liquor.

EXAMPLE 3

This experiment is similar to Example 1, except that 50 ml of dimethylformamide is employed.

Yield: 131 g (49% in reference to tripropylamine).

EXAMPLE 4

The experiment is similar to Example 1, except that 600 ml of dimethylformamide is used.

Yield: 115 g (93% in reference to tripropylamine).

EXAMPLE 5

125 g (1 mole) of propyl bromide and 140 g (0.96 moles) of tripropylamine are heated together with 200 ml of nitromethane with stirring for 12 hours at 50° C. Upon cooling the resulting solution, crystals of tetrapropylammonium bromide precipitated. The crystals are filtered and dried.

Yield: 121 g (47.5% referred to tripropylamine).

When the mother liquor is concentrated, another 92 g (36% in reference to tripropylamine) of tetrapropylammonium bromide can be isolated.

ILLUSTRATIVE APPLICATION 643 g of water glass (375.6 g/l of $SiO_2$, 109.8 g/l of $Na_2O$) are dissolved in 2 liters of water. There are added under stirring 14.5 g of sodium aluminate dissolved in 500 ml water, 41.5 g of sulfuric acid (96% by weight) dissolved in 500 ml of water and 33 g of tetrapropylammonium bromide of Example 1, dissolved in 100 ml water.

The resulting gel is put into a steel autoclave and is crystallized at 150° C. for 78 hours. Upon termination of crystallization, the product is filtered, washed, dried at 120° C. and then is calcined at 500° C. for 24 hours. The formed aluminosilicate is a well-crystallized product evincing the X-ray diffraction lines of the known zeolite ZSM-5.

The foregoing examples are presented for purposes of illustration only and are not to be considered as limiting the invention.

We claim:

1. A method for producing tetrapropylammonium bromide comprising reacting tripropylamine with propyl bromide in dimethylformamide at a temperature between 60° and 160 C.

* * * * *